US00PP36845P2

(12) United States Plant Patent
Mathey

(10) Patent No.: US PP36,845 P2
(45) Date of Patent: Jul. 22, 2025

(54) ***DIERVILLA* PLANT NAMED 'SMNDSF'**

(50) Latin Name: ***Diervilla* x *splendens***
Varietal Denomination: SMNDSF

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/947,584

(22) Filed: Nov. 14, 2024

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Diervilla* plant named 'SMNDSF', characterized by its relatively compact, upright to outwardly spreading and mounding plant habit; vigorous growth habit and rapid growth rate; freely branching habit; dense and bushy appearance; dark red-colored stems; leaves that are bronze orange in color in the spring becoming closer to yellow green in color during the summer; numerous greenish yellow-colored flowers; and good garden performance.

3 Drawing Sheets

Figure 1:
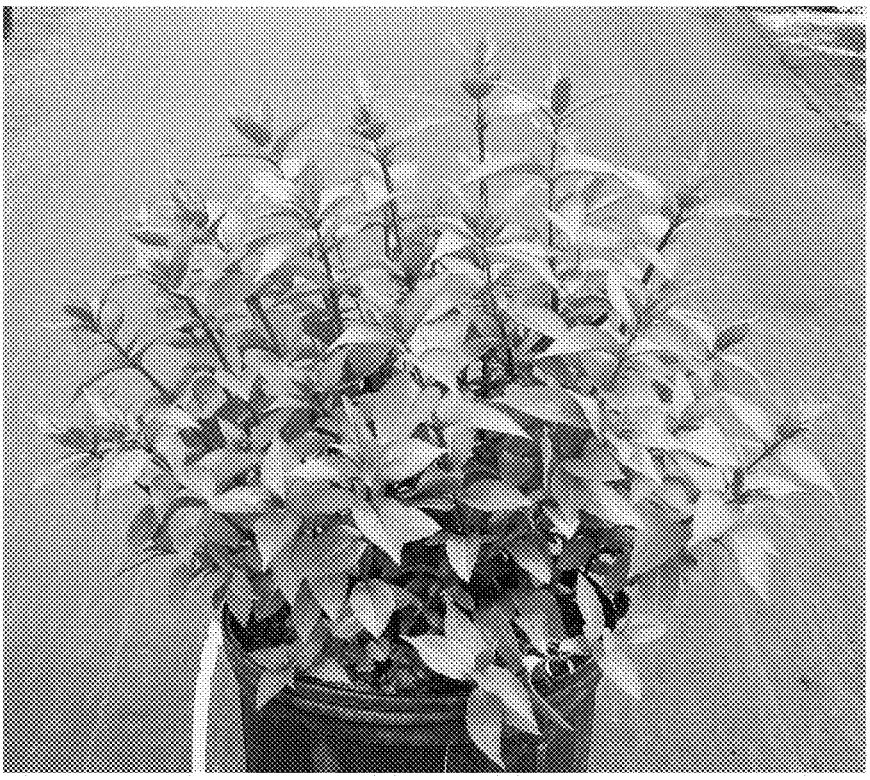

Botanical designation: *Diervilla* x *splendens*.
Cultivar denomination: 'SMNDSF'.

BACKGROUND OF THE INVENTION

The present invention relates to a new and distinct cultivar of *Diervilla* plant, botanically known as *Diervilla* x *splendens*, commonly referred to as Bush Honeysuckle and hereinafter referred to by the cultivar name 'SMNDSF'.

The new *Diervilla* is a product of a planned breeding program conducted by the Inventor in Grand Haven, Michigan. The objective of the breeding program was to develop new freely branching *Diervilla* plants with attractive and vibrant leaf coloration.

The new *Diervilla* plant originated from an open-pollination in 2020 in Grand Haven, Michigan of an unidentified proprietary selection of *Diervilla* x *splendens*, not patented, as the female, or seed, parent with an unknown proprietary selection of *Diervilla* x *splendens* as the male, or pollen, parent. The new *Diervilla* plant was discovered and selected by the Inventor in 2021 as a single flowering plant within the progeny of the stated open-pollination in a controlled environment in Grand Haven, Michigan.

Asexual reproduction of the new *Diervilla* plant by softwood stem cuttings in a controlled greenhouse environment in Grand Haven, Michigan since 2021 has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDSF'. These characteristics in combination distinguish 'SMNDSF' as a new and distinct *Diervilla* plant:

1. Relatively compact, upright to outwardly spreading and mounding plant habit.
2. Vigorous growth habit and rapid growth rate.
3. Freely branching habit; dense and bushy appearance.
4. Dark red-colored stems.
5. Leaves that are bronze orange in color in the spring becoming closer to yellow green in color during the summer.
6. Numerous greenish yellow-colored flowers.
7. Good garden performance.

Plants of the new *Diervilla* can be compared to plants of the female parent selection. In side-by-side comparisons, plants of the new *Diervilla* differ primarily from plants of the female parent selection in leaf color as leaves of plants of the new *Diervilla* are bronze orange in color in the spring and becoming closer to yellow green in color during the summer whereas leaves of plants of the female parent selection are yellow in color.

Plants of the new *Diervilla* can be compared to plants of *Diervilla* x *splendens* 'G2X88544', disclosed in U.S. Plant Pat. No. 27,548. In side-by-side comparisons, plants of the new *Diervilla* differ primarily from plants of 'G2X88544' in the following characteristics:

1. Plants of the new *Diervilla* are shorter than plants of 'G2X88544'.
2. Plants of the new *Diervilla* are more mounded and denser than and not as open as plants of 'G2X88544'.
3. During the spring, leaves of plants of the new *Diervilla* are brighter orange in color than leaves of plants of 'G2X88544'.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet (FIG. 1) is a side perspective view of a typical plant of 'SMNDSF' grown in a container.

Figure 2:
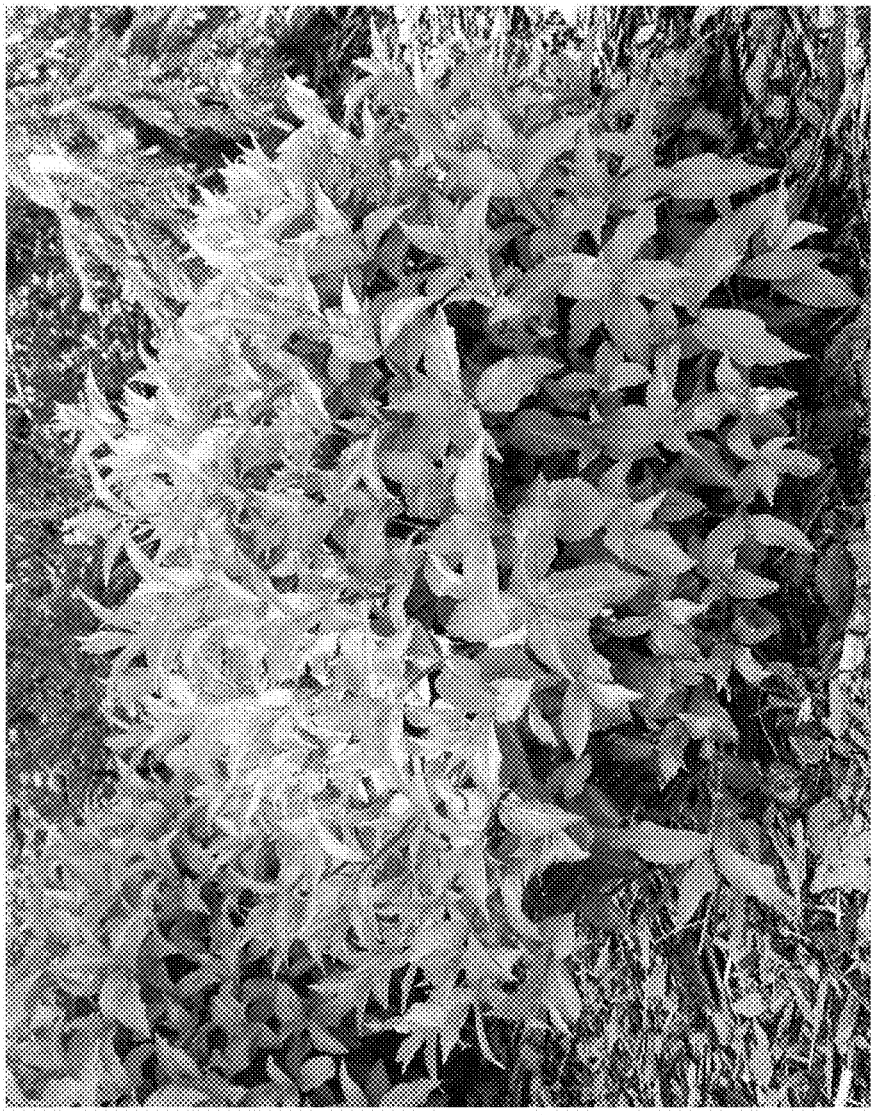

The photograph on the second sheet (FIG. 2) is a side perspective view of a typical plant of 'SMNDSF' grown in an outdoor nursery.

Figure 3:
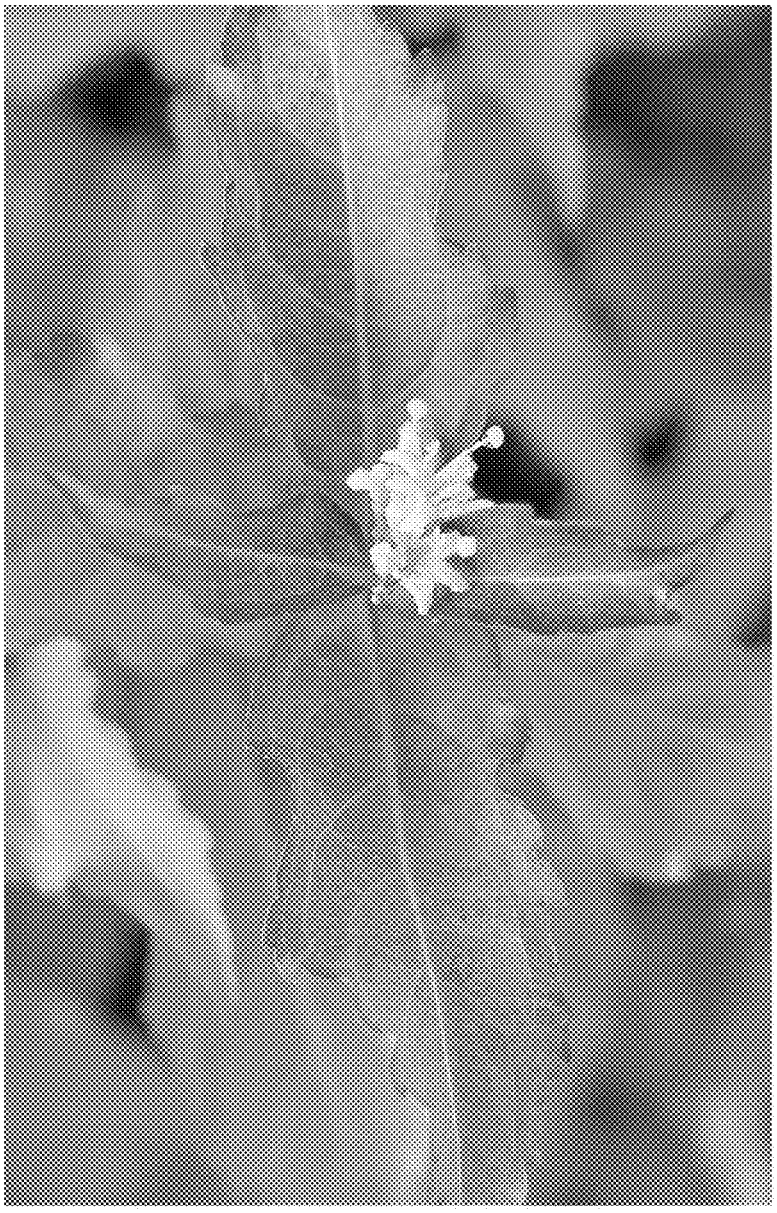

The photograph on the third sheet (FIG. 3) is close-up view of a typical flowering stem of 'SMNDSF'.

DETAILED BOTANICAL DESCRIPTION

The following observations, measurements and values describe plants grown in the late spring and early summer in three-gallon containers in a polyethylene-covered greenhouse in Grand Haven, Michigan and under cultural practices typical of commercial *Diervilla* production. During the production of the plants, day temperatures ranged from 18° C. to 27° C. and night temperatures ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Diervilla* x *splendens* 'SMNDSF'.

Parentage:

- *Female, or seed, parent*.—Unidentified proprietary selection of *Diervilla* x *splendens*, not patented.
- *Male, or pollen, parent*.—Unknown proprietary selection of *Diervilla* x *splendens*, not patented.

Propagation:

- *Type*.—By softwood stem cuttings.
- *Time to initiate roots, summer*.—About 10 to 21 days at temperatures ranging from about 18° C. to 27° C.
- *Time to produce a rooted young plant, summer*.—About four weeks at temperatures ranging from about 18° C. to 27° C.
- *Root description*.—Medium in thickness to thick; fleshy to fibrous; typically white to tan in color, actual color of the roots is dependent on substrate composition, water quality, fertilizer, substrate temperature and physiological age of roots.
- *Rooting habit*.—Moderately freely branching; medium density.

Plant description:

- *Plant form and growth habit*.—Perennial deciduous shrub; relatively compact, upright to outwardly spreading and mounding plant habit; vigorous growth habit and rapid growth rate.
- *Branching habit*.—Freely branching habit; dense and bushy appearance with about 20 to 25 lateral branches developing per plant; pinching will enhance lateral branch development.
- *Plant height*.—About 80 cm.
- *Plant diameter* (*area of spread*).—About 75 cm.

Lateral branch description:

- *Length*.—About 70 cm.
- *Diameter*.—About 5 mm.
- *Internode length*.—About 4.5 cm.
- *Aspect*.—About 15° to 60° from vertical.
- *Strength*.—Strong.
- *Texture*.—Smooth, glabrous; becoming woody with development; longitudinally ridged.
- *Color, developing, upper and lower surfaces*.—Close to 183C.
- *Color, when woody, upper and lower surfaces*.—Close to 199C.

Leaf description:

- *Arrangement*.—Opposite, simple.
- *Length*.—About 7.3 cm.
- *Width*.—About 3.75 cm.
- *Shape*.—Elliptic to ovate.
- *Apex*.—Acuminate.
- *Base*.—Obtuse.
- *Margin*.—Serrate.
- *Texture, upper surface*.—Smooth, glabrous.
- *Texture, lower surface*.—Smooth, glabrous with prominent midrib.
- *Venation pattern*.—Pinnate.
- *Color*.—Developing leaves, during spring, upper surface: Close to 166D. Developing leaves, during spring, lower surface: Close to 166B. Fully expanded leaves, during the summer, upper and lower surfaces: Close to 166D and proximally, close to 146C; color becoming closer to 136B with development; venation, close to 183C and distally, close to 144D.
- *Petioles*.—Length: About 5 mm. Diameter: About 2 mm. Texture, upper and lower surfaces: Smooth, glabrous. Color, upper and lower surfaces: Close 183C.

Flower description:

- *Flower appearance and arrangement*.—Salverform flowers arranged in terminal and axillary bipartite cymes; freely flowering habit with about seven flowers per inflorescence with numerous inflorescences developing per plant; flowers face upright to outwardly.
- *Fragrance*.—None detected.
- *Natural flowering season*.—Plants flower during the summer in Michigan.
- *Flower longevity*.—Individual flowers last about one to two weeks on the plant; flowers not persistent.
- *Flower buds*.—Length: About 1 cm. Diameter: About 2 mm. Shape: Oblong. Color: Close to 144C.
- *Inflorescence diameter*.—About 2 cm.
- *Inflorescence height*.—About 2 cm.
- *Flower diameter*.—About 1 cm.
- *Flower length*.—About 1.25 cm.
- *Flower throat diameter*.—About 3 mm.
- *Flower tube length*.—About 6 mm.
- *Flower tube diameter, proximally*.—About 2 mm.
- *Petals*.—Quantity and arrangement: Five fused with apices free and reflexing. Lobe length: About 5 mm. Lobe width: About 2 mm. Lobe shape: Narrowly elliptic to oblong. Lobe apex: Obtuse. Lobe margin: Entire. Lobe texture, upper and lower surfaces: Smooth, silky; glabrous. Throat texture: Smooth, glabrous. Tube texture: Smooth, glabrous. Color: When opening and fully opened, upper surface: Close to 151C; throat, close to 151C. When opening and fully opened, lower surface: Close to 151C; tube, close to 151C.

*Sepals*.—Quantity and arrangement: Five in a single whorl fused at the base into a stellate-shaped calyx. Length: About 2 mm. Width: Less than 1 mm. Shape: Acicular. Apex: Acute. Margin: Entire. Texture, upper and lower surfaces: Smooth, glabrous. Color, upper and lower surfaces: Close to 144C.

*Peduncles*.—Length: About 5 mm. Diameter: About 1 mm. Aspect: About 45° from the stem axis. Strength: Strong. Texture: Smooth, glabrous. Color, upper surface: Close to 183C. Color, lower surface: Close to 144C.

*Pedicels*.—Length: About 3 mm. Diameter: Less than 1 mm. Aspect: About 45° from peduncle axis. Strength: Strong. Texture: Smooth, glabrous. Color, upper surface: Close to 183C. Color, lower surface: Close to 144C.

*Reproductive organs*.—Stamens: Quantity per flower: Five. Filament length: About 5 mm. Filament color: Close to N144A. Anther length: About 2 mm. Anther shape: Linear. Anther color: Close to 13A. Pollen amount: Moderate. Pollen color: Close to 13D. Pistils: Quantity per flower: One. Pistil length: About 2 cm. Stigma shape: Peltate. Stigma color: Close to 144A. Style length: About 1.9 cm. Style color: Close to N144A. Ovary color: Close to 144A. Fruits: Length: About 1 cm. Diameter: About 2.5 mm. Shape: Oblong. Color: Close to N199B. Seeds: Length: About 1 mm. Diameter: About 1 mm. Color: Close to N199D.

Garden performance: Plants of the new *Diervilla* have been observed to have good garden performance and tolerate rain, wind and to be suitable for USDA Hardiness Zones 3 through 8.

Pathogen & pest resistance: To date, plants of the new *Diervilla* have not been shown to be resistant to pathogens and pests common to *Diervilla* plants.

It is claimed:

1. A new and distinct *Diervilla* plant named 'SMNDSF' as herein illustrated and described.

* * * * *